United States Patent
Lacki (10) Patent No.: US 9,551,694 B2
(45) Date of Patent: Jan. 24, 2017

(54) MICRO TITRE PLATE (75) Inventor: Karol Lacki, Uppsala (SE)

(73) Assignee: GE Healthcare BioProcess R&D AB, Uppsala (SE)

(*) Notice: Subject to any disclaimer, the term of this patent is extended or adjusted under 35 U.S.C. 154(b) by 1067 days.

(21) Appl. No.: 13/122,585

(22) PCT Filed: Oct. 7, 2009

(86) PCT No.: PCT/SE2009/051113
§ 371 (c)(1),
(2), (4) Date: Apr. 5, 2011

(87) PCT Pub. No.: WO2010/044727
PCT Pub. Date: Apr. 22, 2010

(65) Prior Publication Data
US 2011/0195517 A1    Aug. 11, 2011

(30) Foreign Application Priority Data
Oct. 15, 2008   (SE) ...................... 0802199

(51) Int. Cl.
G01M 1/00 (2006.01)
B01D 21/00 (2006.01)
B65D 1/04 (2006.01)
G01N 30/86 (2006.01)
B01L 3/00 (2006.01)
G01N 30/46 (2006.01)
G01N 30/60 (2006.01)

(52) U.S. Cl.
CPC ....... *G01N 30/8658* (2013.01); *B01L 3/50255* (2013.01); *B01L 2300/069* (2013.01); *G01N 30/466* (2013.01); *G01N 30/6043* (2013.01); *Y10T 436/25* (2015.01)

(58) Field of Classification Search
CPC ... B01L 3/50255; B01L 3/5023; B01L 3/5085; B01L 2300/069; G01N 30/8658; G01N 1/405
See application file for complete search history.

(56) References Cited

U.S. PATENT DOCUMENTS 4,587,212 A * 5/1986 Baker ............................ 435/7.9
6,265,224 B1 * 7/2001 Collis et al. ................... 436/178

FOREIGN PATENT DOCUMENTS

| WO | WO 02/089982 | 11/2002 |
| WO | WO 2005/021130 | 3/2005 |
| WO | WO 2007/144353 | 12/2007 |

OTHER PUBLICATIONS

Berganger, Tryggve et al. "High-throughput process development: determination of dynamic binding capacity using microtitre filter plates filled with chromatography resin." Biotechnol. Prog. (2008) 24 632-639.*
Scordino, Monica et al. "Adsorption of flavonoids on resins: cyanidin 3-glucoside." J. Agric. Food Chem (2004) 52 1965-1972.*
GE Healthcare. "PreDictor plates." High-throughput process development. Instructions 28-9258-34 AD. Nov. 2008.*

(Continued)

*Primary Examiner* — Christopher A Hixson
(74) *Attorney, Agent, or Firm* — Wood IP LLC (57) ABSTRACT A micro titer plate comprising a number of wells filled with separation matrix. According to the invention the volume of the separation matrix is varied between at least some of the wells.

6 Claims, 8 Drawing Sheets

|   | 1 | 2 | 3 | 4 | 5 | 6 | 7 | 8 | 9 | 10 | 11 | 12 |
|---|---|---|---|---|---|---|---|---|---|----|----|----|
| A | $V_1$ | $V_1$ | $V_2$ | $V_2$ | $V_3$ | $V_3$ | $V_4$ | $V_4$ | $V_5$ | $V_5$ | $V_6$ | $V_6$ |
| B | $V_1$ | $V_1$ | $V_2$ | $V_2$ | $V_3$ | $V_3$ | $V_4$ | $V_4$ | $V_5$ | $V_5$ | $V_6$ | $V_6$ |
| C | $V_1$ | $V_1$ | $V_2$ | $V_2$ | $V_3$ | $V_3$ | $V_4$ | $V_4$ | $V_5$ | $V_5$ | $V_6$ | $V_6$ |
| D | $V_1$ | $V_1$ | $V_2$ | $V_2$ | $V_3$ | $V_3$ | $V_4$ | $V_4$ | $V_5$ | $V_5$ | $V_6$ | $V_6$ |
| E | $V_1$ | $V_1$ | $V_2$ | $V_2$ | $V_3$ | $V_3$ | $V_4$ | $V_4$ | $V_5$ | $V_5$ | $V_6$ | $V_6$ |
| F | $V_1$ | $V_1$ | $V_2$ | $V_2$ | $V_3$ | $V_3$ | $V_4$ | $V_4$ | $V_5$ | $V_5$ | $V_6$ | $V_6$ |
| G | $V_1$ | $V_1$ | $V_2$ | $V_2$ | $V_3$ | $V_3$ | $V_4$ | $V_4$ | $V_5$ | $V_5$ | $V_6$ | $V_6$ |
| H | $V_1$ | $V_1$ | $V_2$ | $V_2$ | $V_3$ | $V_3$ | $V_4$ | $V_4$ | $V_5$ | $V_5$ | $V_6$ | $V_6$ |

(56) References Cited

OTHER PUBLICATIONS

Ljunglof, Anders et al. "Measurement of ligand distribution in individual adsorbent particles using confocal scanning laser microscopy and confocal micro-Raman spectroscopy." Journal of Chromatography A (2000) 893 235-244.*
Bergander, T., et al., Biotechnol. Prog., 24, 632-639 (2008).
Neng-Hua, G., et al., Journal of Biological Chemistry, 267(27), 19349-19355 (1992).
Ljunglof, A., et al., Journal of Chromatography A, 893, 235-244 (2000).
Currie, D., Biometrics, 38(4), 907-919 (1982).
Coffman, J., et al., Biotechnology and Bioengineering, 100:4 (2008) 605-618.
Schweich, D., et al., Journal of Hydrology, 50 (1981) 1-33.
Wierling, P., et al., Chemie Ingenieur Technik, 77:8 (2005) 1240.
Extended EP Search Report Issued on Corresponding EP Patent Application No. 09820836.6 Dated Oct. 24, 2012.

* cited by examiner

Figure 1

|   | A | B | C | D | E | F | G | H |
|---|---|---|---|---|---|---|---|---|
| 12 | $V_6$ | $V_6$ | $V_6$ | $V_6$ | $V_6$ | $V_6$ | $V_6$ | $V_6$ |
| 11 | $V_6$ | $V_6$ | $V_6$ | $V_6$ | $V_6$ | $V_6$ | $V_6$ | $V_6$ |
| 10 | $V_5$ | $V_5$ | $V_5$ | $V_5$ | $V_5$ | $V_5$ | $V_5$ | $V_5$ |
| 9 | $V_5$ | $V_5$ | $V_5$ | $V_5$ | $V_5$ | $V_5$ | $V_5$ | $V_5$ |
| 8 | $V_4$ | $V_4$ | $V_4$ | $V_4$ | $V_4$ | $V_4$ | $V_4$ | $V_4$ |
| 7 | $V_4$ | $V_4$ | $V_4$ | $V_4$ | $V_4$ | $V_4$ | $V_4$ | $V_4$ |
| 6 | $V_3$ | $V_3$ | $V_3$ | $V_3$ | $V_3$ | $V_3$ | $V_3$ | $V_3$ |
| 5 | $V_3$ | $V_3$ | $V_3$ | $V_3$ | $V_3$ | $V_3$ | $V_3$ | $V_3$ |
| 4 | $V_2$ | $V_2$ | $V_2$ | $V_2$ | $V_2$ | $V_2$ | $V_2$ | $V_2$ |
| 3 | $V_2$ | $V_2$ | $V_2$ | $V_2$ | $V_2$ | $V_2$ | $V_2$ | $V_2$ |
| 2 | $V_1$ | $V_1$ | $V_1$ | $V_1$ | $V_1$ | $V_1$ | $V_1$ | $V_1$ |
| 1 | $V_1$ | $V_1$ | $V_1$ | $V_1$ | $V_1$ | $V_1$ | $V_1$ | $V_1$ |

Figure 2

|   | A | B | C | D | E | F | G | H |
|---|---|---|---|---|---|---|---|---|
| 12 | $V_{12}$ | $V_{12}$ | $V_{12}$ | $V_{12}$ | $V_{12}$ | $V_{12}$ | $V_{12}$ | $V_{12}$ |
| 11 | $V_{11}$ | $V_{11}$ | $V_{11}$ | $V_{11}$ | $V_{11}$ | $V_{11}$ | $V_{11}$ | $V_{11}$ |
| 10 | $V_{10}$ | $V_{10}$ | $V_{10}$ | $V_{10}$ | $V_{10}$ | $V_{10}$ | $V_{10}$ | $V_{10}$ |
| 9 | $V_9$ | $V_9$ | $V_9$ | $V_9$ | $V_9$ | $V_9$ | $V_9$ | $V_9$ |
| 8 | $V_8$ | $V_8$ | $V_8$ | $V_8$ | $V_8$ | $V_8$ | $V_8$ | $V_8$ |
| 7 | $V_7$ | $V_7$ | $V_7$ | $V_7$ | $V_7$ | $V_7$ | $V_7$ | $V_7$ |
| 6 | $V_6$ | $V_6$ | $V_6$ | $V_6$ | $V_6$ | $V_6$ | $V_6$ | $V_6$ |
| 5 | $V_5$ | $V_5$ | $V_5$ | $V_5$ | $V_5$ | $V_5$ | $V_5$ | $V_5$ |
| 4 | $V_4$ | $V_4$ | $V_4$ | $V_4$ | $V_4$ | $V_4$ | $V_4$ | $V_4$ |
| 3 | $V_3$ | $V_3$ | $V_3$ | $V_3$ | $V_3$ | $V_3$ | $V_3$ | $V_3$ |
| 2 | $V_2$ | $V_2$ | $V_2$ | $V_2$ | $V_2$ | $V_2$ | $V_2$ | $V_2$ |
| 1 | $V_1$ | $V_1$ | $V_1$ | $V_1$ | $V_1$ | $V_1$ | $V_1$ | $V_1$ |

Figure 3

| | 1 | 2 | 3 | 4 | 5 | 6 | 7 | 8 | 9 | 10 | 11 | 12 |
|---|---|---|---|---|---|---|---|---|---|---|---|---|
| A | $V_1$ | $V_1$ | $V_1$ | $V_1$ | $V_1$ | $V_1$ | $V_1$ | $V_1$ | $V_1$ | $V_1$ | $V_1$ | $V_1$ |
| B | $V_2$ | $V_2$ | $V_2$ | $V_2$ | $V_2$ | $V_2$ | $V_2$ | $V_2$ | $V_2$ | $V_2$ | $V_2$ | $V_2$ |
| C | $V_3$ | $V_3$ | $V_3$ | $V_3$ | $V_3$ | $V_3$ | $V_3$ | $V_3$ | $V_3$ | $V_3$ | $V_3$ | $V_3$ |
| D | $V_4$ | $V_4$ | $V_4$ | $V_4$ | $V_4$ | $V_4$ | $V_4$ | $V_4$ | $V_4$ | $V_4$ | $V_4$ | $V_4$ |
| E | $V_5$ | $V_5$ | $V_5$ | $V_5$ | $V_5$ | $V_5$ | $V_5$ | $V_5$ | $V_5$ | $V_5$ | $V_5$ | $V_5$ |
| F | $V_6$ | $V_6$ | $V_6$ | $V_6$ | $V_6$ | $V_6$ | $V_6$ | $V_6$ | $V_6$ | $V_6$ | $V_6$ | $V_6$ |
| G | $V_7$ | $V_7$ | $V_7$ | $V_7$ | $V_7$ | $V_7$ | $V_7$ | $V_7$ | $V_7$ | $V_7$ | $V_7$ | $V_7$ |
| H | $V_8$ | $V_8$ | $V_8$ | $V_8$ | $V_8$ | $V_8$ | $V_8$ | $V_8$ | $V_8$ | $V_8$ | $V_8$ | $V_8$ |

Figure 4

| | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ |
|---|---|---|---|---|---|---|---|---|---|---|---|---|
| Figure 1 | 2 | 4 | 6 | 8 | 20 | 50 | | | | | | |
| Figure 3 | 2 | 4 | 6 | 8 | 10 | 20 | 40 | 80 | | | | |
| Figure 2 | 2 | 4 | 6 | 8 | 10 | 15 | 20 | 30 | 40 | 60 | 80 | 100 |

Figure 6, Table E1

| # of gel volumes | Resin volume uL | | | |
|---|---|---|---|---|
| 1  | 43 | 47 | 53 |
| 2  | 24 | 28 | 36 |
| 3  | 18 | 21 | 27 |
| 4  | 16 | 18 | 22 |
| 5  | 13 | 16 | 19 |
| 6  | 4  | 14 | 17 |
| 7  |    | 11 | 16 |
| 8  |    | 3  | 15 |
| 9  |    |    | 14 |
| 10 |    |    | 12 |
| 11 |    |    | 8  |
| 12 |    |    | 2  |

Figures 7a, 7b, 7c

Initial concentration: Co = 4 g/L

MICRO TITRE PLATE

CROSS-REFERENCE TO RELATED APPLICATIONS

This application is a filing under 35 U.S.C. §371 and claims priority to international patent application number PCT/SE2009/051113 filed Oct. 7, 2009, published on Apr. 22, 2010 as WO 2010/044727, which claims priority to application number 0802199-0 filed in Sweden on Oct. 15, 2008.

FIELD OF THE INVENTION

The present invention relates to micro titre plates of the type mentioned in the preamble of the independent claim 1 and to methods for high throughput screening of adsorption systems including methods for determination of adsorption isotherms.

BACKGROUND OF THE INVENTION

Multiwell plates, also called micro titre plates, have been used for many years in laboratories for the simultaneous analysis of a number of samples. Typical formats include 4, 24, 48, 96 and 384 wells per plate. Initially, these plates had solid bases and liquid samples were pipetted into and out of the wells.

Subsequently, plates with wells provided with a lower well through hole (known as a "drip" if it is provided with downward protruding lips) pierced through the bottom surface. These micro titre plates allowed the samples to flow through the wells which permitted larger sample volumes to be processed (since the sample size was no longer limited to the capacity of the well).

Later developments of micro titre plates were provided with filter or membrane wells in which each well was provided with a microporous filter or membrane which extended over the cross-section of the well such that all of the sample passing through the well had to pass through the filter or membrane. These micro titre plates are also called micro titre filter plates.

A further development of a micro titre plate comprises wells with a lower well through hole or drip and a filter or membrane and which wells are each at least partly filled with a media such as a chromatographic gel or slurry or chromatographic particles.

Different screening processes that could be performed on such micro titre plates are for example screening of/for: i) conditions for optimal binding capacity, ii) most efficient wash buffers for washing off impurities from chromatography resin; iii) most efficient eluting solution; iv) selectivity obtained using different ligands, v) best resin either from capacity or purity perspective. Considering the multi well format of microtiter plates, if processes under different conditions need to be studied there are different possibilities to change conditions on a single plate. For example the concentration of the sample added can be changed, the composition of the buffer in which the sample is dissolved can be changed, the effect of overall time of contact between the sample and a chromatography resin can be studied, or any combinations of the above.

High throughput studies of chromatographic separations using microtiter plates filled with chromatography resin proved highly efficient in reducing time and sample requirements necessary for development of large scale purification processes. While the studies reported have focused on specific aspects of chromatographic steps, a very few studies have been reported focusing on understanding physics of the separation processes studied. From understanding the separation process perspective the knowledge of adsorption isotherm is of paramount importance. Adsorption isotherms are fundamental property of any separation systems, and an isotherm should always be determined in order to full understand governing principles behind an adsorption process.

SUMMARY OF THE INVENTION

According to the present invention, an improved micro titre plate filled with a separation matrix according to the characterising part of claim 1 is provided.

Hereby the user can add the same volume of sample having the same concentration and still obtain data pertaining to different saturation of separation matrix with the sample because of the different media volumes in different wells.

Suitably the different media volumes are chosen based on a specific algorithm assuring the highest possible quality of the data obtained with respect to describing of adsorption equilibria for the system studied.

Further suitable embodiments are described in the dependent claims.

Furthermore a method for determining an adsorption isotherm is provided according to claim 10.

Furthermore the use of a micro titre plate according to the invention for determining adsorption isotherms is described.

DETAILED DESCRIPTION OF THE INVENTION

A multiwell plate, also called a micro titre filter plate or micro titre plate, that is filled with a separation matrix is provided. The separation matrix could be a chromatography media and it can also be called for example a solid phase, resin, gel or adsorber. The number of wells in the plate is in a first embodiment of the invention 96. Other numbers are however also possible such as 24, 48, and 384. According to the invention at least some of the wells of the plate are filled with well defined different amounts of separation matrix. The distribution of separation matrix in the different wells can be different for different uses of the plate. Micro titre plates are used for the screening of different chromatographic attributes such as for example determination of binding capacities, effectiveness of wash buffer in removal of impurities, effect of different buffer conditions on selectivity (a relative difference between capacities for different solutes adsorbing on the solid phase) or for studying the effect of solute concentration in the liquid phase on the amount of solute adsorbed on the solid phase, a so called adsorption isotherms studies. For a person skilled in the art of chromatography it is known that adsorption isotherm is a fundamental concept for describing adsorption processes, including all the processes listed above. According to the invention it has been shown that for the study of adsorption isotherm it is beneficial to have a distribution of different volumes of separation matrix in at least some of the different wells. A correctly chosen distribution of different volumes in a plate enables collection of adsorption data which quality will be sufficient to describe an adsorption isotherm in the most effective manner using the smallest number of data points necessary.

Figure 1:
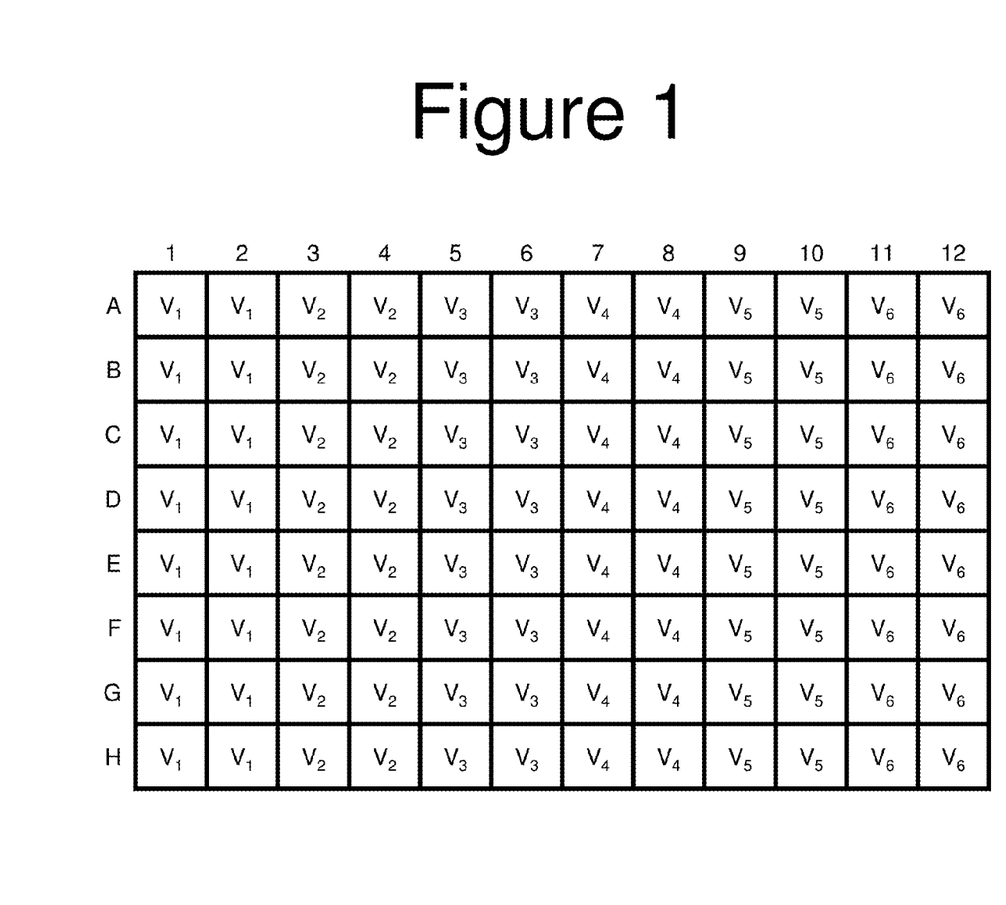
FIG. 1 is a schematic view of a micro titre plate filled with separation matrix according to a first embodiment of the invention.

A first embodiment of the invention is shown in FIG. 1. In this example a 96 wells plate is used and there are six different volumes of separation matrix in the wells. The two first columns have in this example the same volume of separation matrix in all wells. The two next columns have the same volume of separation matrix in each well but this volume is different from the first volume etc. according to FIG. 1.

Figure 2:
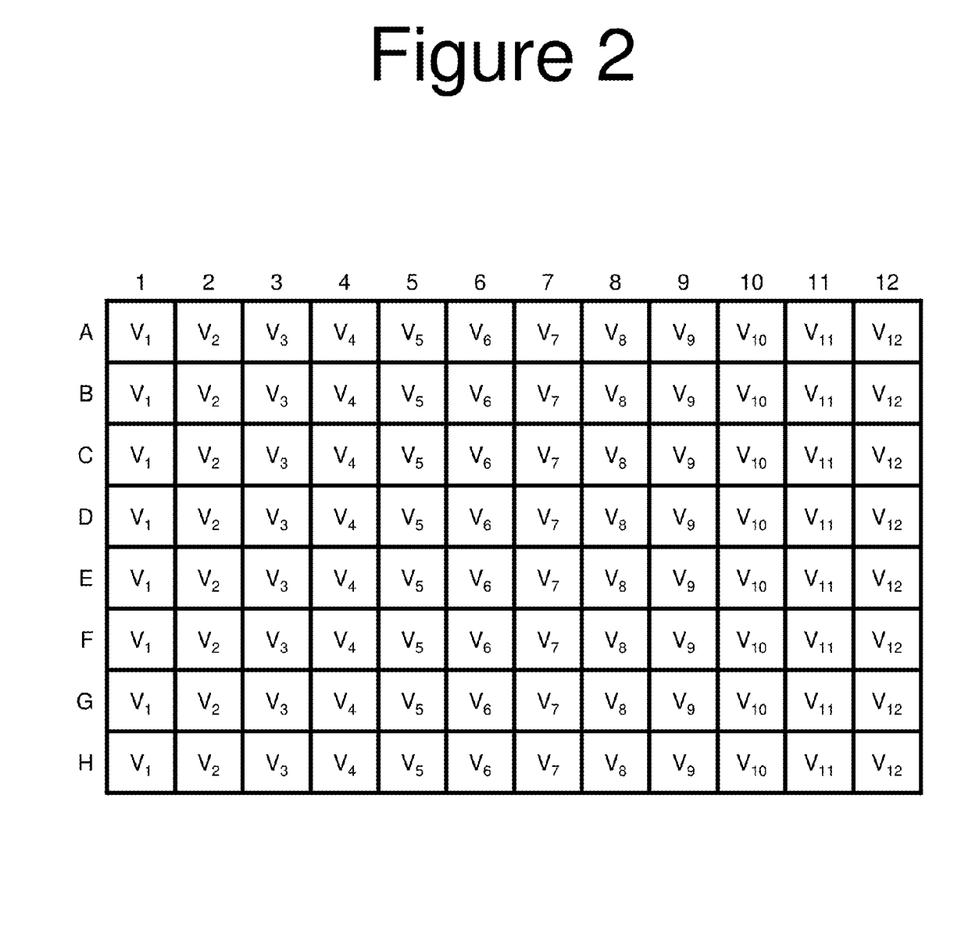
FIG. 2 is a schematic view of a micro titre plate filled with separation matrix according to a second embodiment of the invention.

FIG. 2 is another example of an advantageous distribution. Here there are 12 different volumes of separation matrix. The volume of separation matrix is the same in all wells in the same column. But the volume differs between the columns according to FIG. 2.

Figure 3:
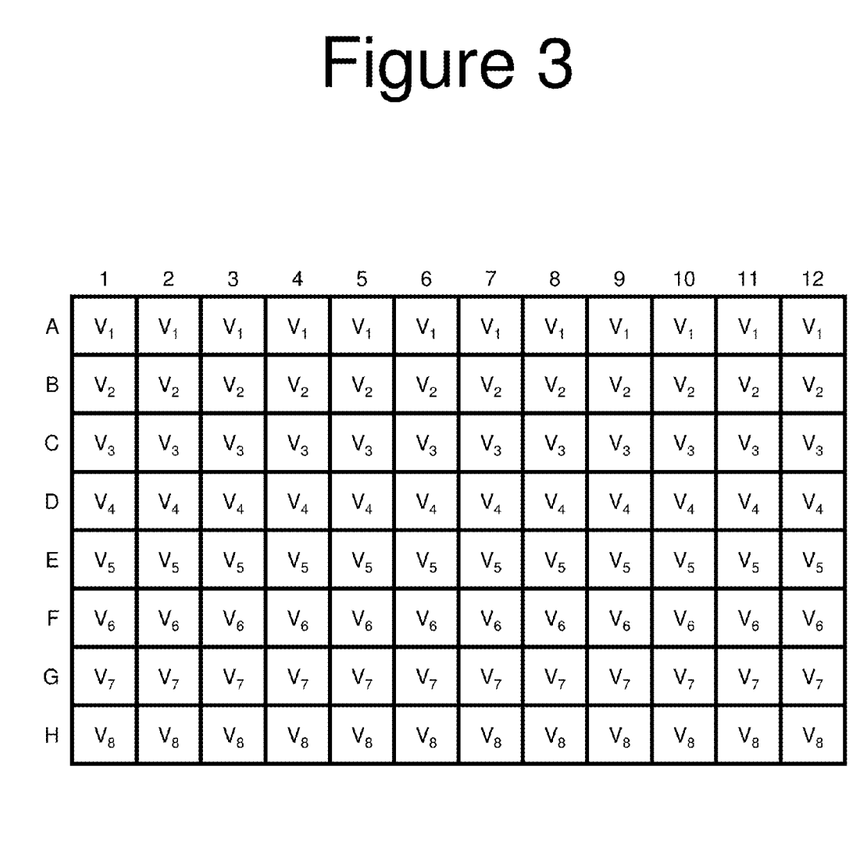
FIG. 3 is a schematic view of a micro titre plate filled with separation matrix according to a third embodiment of the invention.

FIG. 3 is a further example of distribution. Here each row has the same volume of separation matrix in all its wells and all rows have different volumes of separation matrix.

Figure 4:
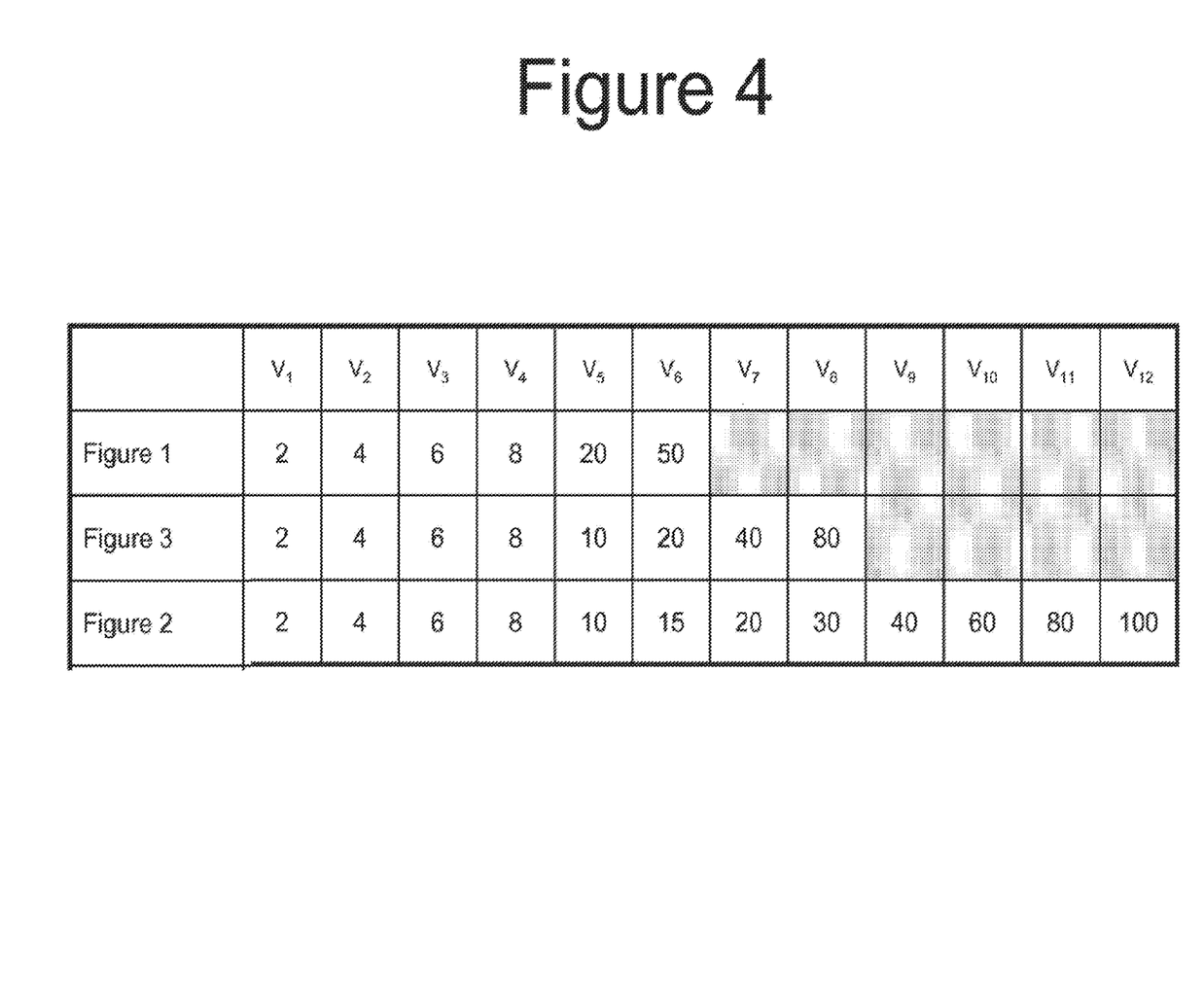
FIG. 4 shows an example of separation matrix volume distributions for the plate layouts shown in FIG. 1-3.

FIG. 4 is an example of separation matrix volume distributions for the plate layouts shown in FIG. 1-3. These numbers are only meant to be used as an example and should not be limiting the scope of the invention.

Adsorption isotherm describes thermodynamic of adsorption process studies, and therefore, is a fundamental property of any protein separation system. This knowledge about the type of isotherm responsible for a separation is a prerequisite to correctly describe the separation.

Figure 5A:
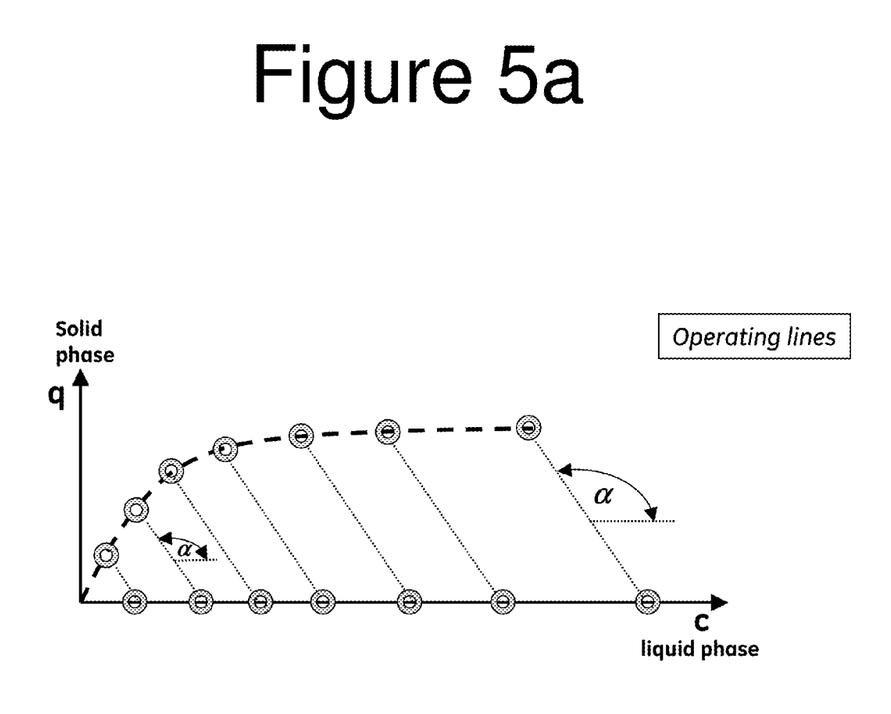
FIG. 5a is a diagram showing the principle for obtaining an adsorption isotherm using constant separation matrix volume.

Among many methods for determination of adsorption isotherms a method based on batch adsorption is fairly popular. In this method a well defined volume of separation matrix and sample are brought in contact with each other and after equilibrium is reached between concentrations in the liquid and solid phases these concentrations are measured and a single point on the adsorption isotherm is obtained. In order to obtain more points either ratio of separation matrix to sample volume or sample concentration need to be changed. While changing sample volume is fairly easy there may be limitations related to a total volume of a system available for experiments. Changing separation matrix volume is also difficult and special methods need to be developed to have a full control over the resin volume used. Changing sample concentration seems easy but only if composition of bulk liquid is known. If the composition is complex, changing sample concentration without changing the composition is close to impossible for most of practical situations, especially if the concentration needs to be increased. FIG. 5a shows a diagram of an adsorption isotherm achieved by using the same solid phase volume and changing the sample concentration. The x-axis is concentration in liquid phase and the y-axis is concentration in solid phase. From each starting point with different sample concentration a single point on the adsorption isotherm is achieved when equilibration is reached. The operating lines shown in FIG. 5a are a graphical representation of mass balance over a single well. The operating line originates at the point representing initial state of the system and ends at the point representing the equilibrium state given by the adsorption isotherm. The phase ratio, Vliq/Vsolid is the slope of the operating line.

Figure 5B:
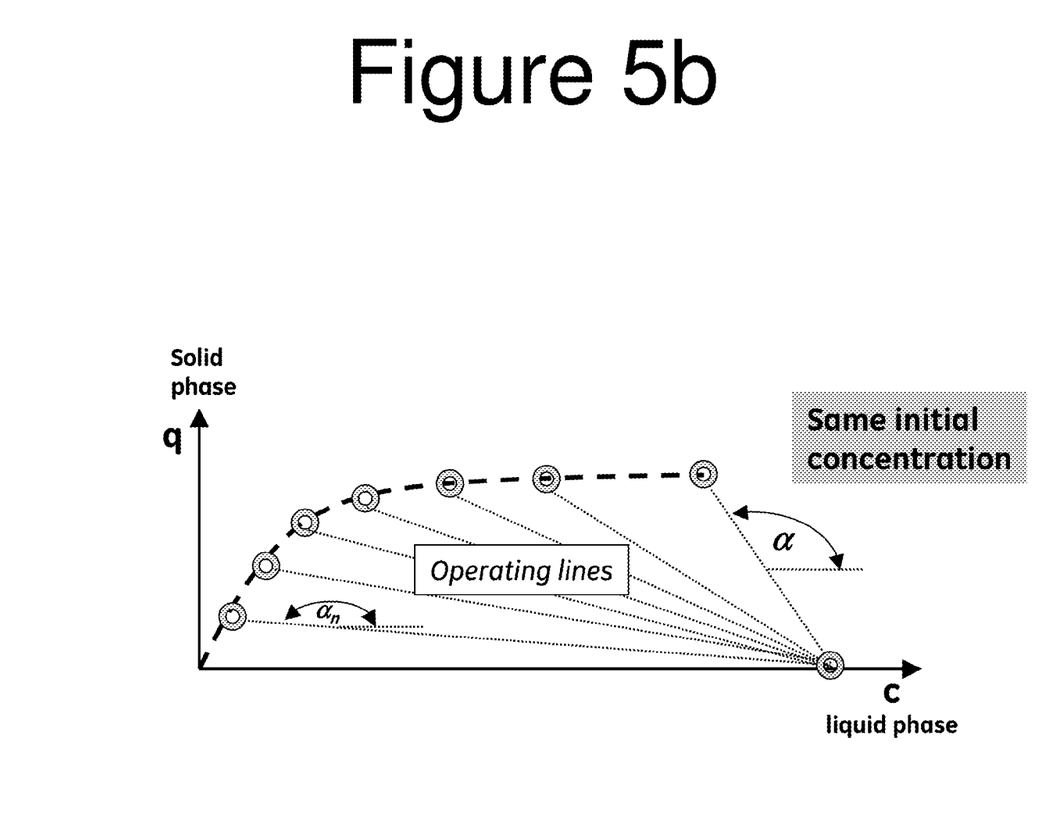
FIG. 5b is a diagram showing the principle for obtaining an adsorption isotherm using the present invention.

According to the invention plates are provided with different separation matrix volumes in the wells as described above. In FIG. 5b the method of achieving an adsorption isotherm from such a plate is shown. The same sample concentration and volume is used all the time but different points on the adsorption isotherm will still be achieved because of the different operating lines originating from the fact that the solid phase volume is different.

From mathematical perspective it can be shown that adsorption isotherms are best described by physical models if points on the adsorption isotherm are distributed in a certain fashion. One example could be that each consecutive equilibrium point is obtained at 2 times higher concentration than the preceding point, and that at least 10% of all points should describe isotherm in the region where capacities are lower than 50% of maximum capacity.

Another example of how to distribute the volumes of separation matrix in the micro titre plate can be to provide volumes that when the plate is used for adsorption isotherm measurements with constant volume and concentration of added sample to the wells that will be used will result in an isotherm where concentrations in the liquid phase after the end of the experiment will be distributed according to the following relationship: concentration in liquid phase in one well divided with the concentration in liquid phase in a neighbouring well with different amount of separation matrix will be between 1 and 3 and most preferable 2. When the larger volume is the numerator. See further example 1 below.

According to the invention a method for determining an adsorption isotherm is further provided. The method comprises the steps of:

using a micro titre plate according to the invention as described above;

adding the same volume and concentration of a sample to the number of wells needed for the analysis;

waiting for a predefined period of time, preferably until equilibrium is reached;

measuring concentration of liquid phase and/or solid phase in at least two wells with different volumes of separation matrix.

Furthermore, this invention covers the use of a micro titre plate according to the invention for determining adsorption isotherms.

Furthermore a method of filling a micro titre plate with separation matrix is proposed in this invention. The method comprises the steps of:

determining a suitable distribution of volumes of separation matrix between the wells based on the specific screening process that will be performed;

filling the wells of the micro titre plate with separation matrix according to the to determined suitable distribution.

These plates according to the invention would also be advantageous to use in other screening processes. For example in determination of effect of contact time on binding capacities. Such studies will lead to elucidation of transport mechanism behind protein adsorption, which in turn would lead to ability to mechanistically describe the adsorption process studied.

EXAMPLES

The present examples are provided for illustrative purposes only, and should not be construed as limiting the scope of the present invention as defined by the appended claims. All references given below and elsewhere in the present specification are hereby included herein by reference.

Example 1

From a statistical point of view it is recommended that in order to obtain the most precise values of model parameters describing an adsorption isotherm, batch experiments should be performed applying an experimental design that would result in equilibrium concentrations characterized by a dilution like (geometric) pattern. This can be shown using the following as an example a case of a Langmuir isotherm, given here by Eq. (1), with maximum binding capacity, Qmax, and the dissociation constant, K, as model parameters. Following the work of Currie (1982) who performed extensive testing of the typical designs used to evaluate enzyme kinetic parameters for the Michaelis-Menten type of enzyme kinetics and showed that the modified dilution/geometric design resulted in the most precise values of the model parameters, it can be concluded that similar designs would be applicable for the Langmuir isotherm model because from the mathematical to point of view, the equation describing Michaelis-Menten kinetics is not different from the Langmuir isotherm.

$$q(C) = \frac{Q_{max} C}{K + C} \quad (1)$$

According to Currie (1982), for a sequence of n observations obtained from runs performed at locations described by the form given by Eq. (2), the values of parameters in Eq. (1) that minimise the generalised parameter variance are shown in Table 1.

$$C_i = a r^{i-1} \quad (2)$$

where: $C_i$ stands for the concentration of protein in the i-th run, and the a and r are the parameters.

TABLE 1

| n | a | r |
|---|---|---|
| 6 | 0.601K | 3.45 |
| 8 | 0.508K | 2.52 |
| 12 | 0.434K | 1.84 |

In case of a typical adsorption isotherm experiments using a batch adsorption protocol the following mass balance always holds at each run location $$q_i(C_i) = \beta(C_{0,i} - C_i) \quad (3)$$

where: $\beta$ is a phase ratio defined as $V_L/V_S$; $V_L$ and $V_S$ represents volume of liquid and solid phase, respectively; $q_i(C_i)$ is an equilibrium adsorption capacity for i-th run, $C_{o,i}$ and $C_i$ are initial and equilibrium protein concentrations for i-th run.

Combining Eq. (1) and Eq. (2) and assuming that the sample volume is constant yields Eq. (4) which describes the preferred distribution of phase ratios for a constant sample concentration, $C_0$ case, as a function of number of run locations and the expected shape the adsorption isotherm.

$$V_{solid,i} = V_{samp} \left[ \frac{1}{C_0 - a r^{i-1}} \frac{Q_{max} a r^{i-1}}{K + a r^{i-1}} \right]^{-1} \quad (4)$$

In order to obtain a suitable distribution of $V_{solid}$, an a priori knowledge of values for the dissociation constant K and the maximum equilibrium capacity $Q_{max}$ is needed. Obviously, this is an evident paradox since these parameters are to be found using the above design. In order to circumvent this situation, educated guesses for these parameters need to be used. These guesses, can be based on data pertaining to similar adsorptive systems.

Figure 6:
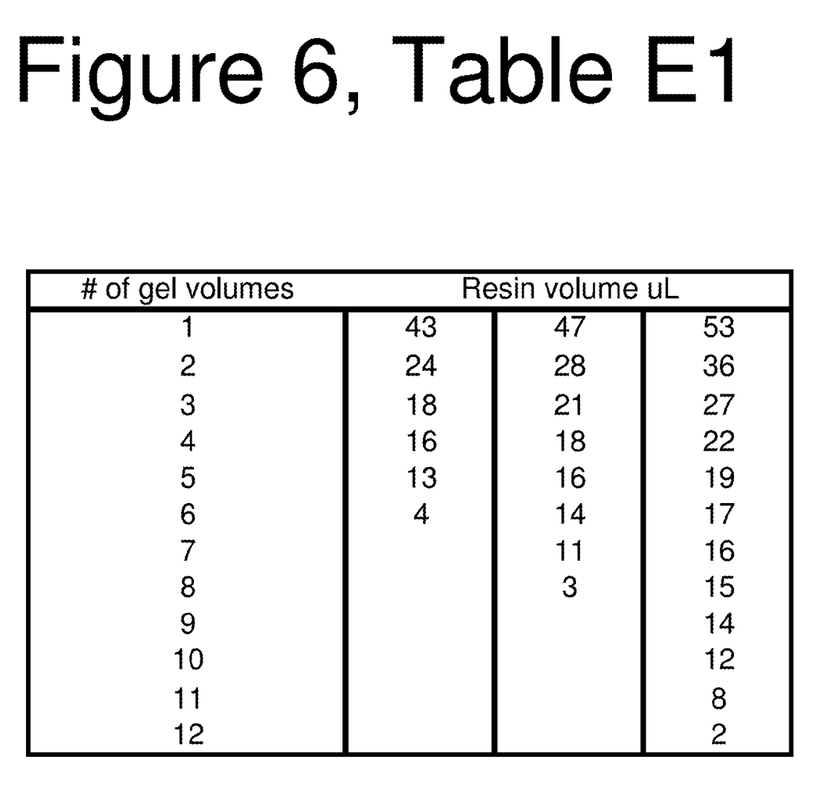
FIG. 6 shows the different separation matrix volumes of Example 1.
Figure 7A:
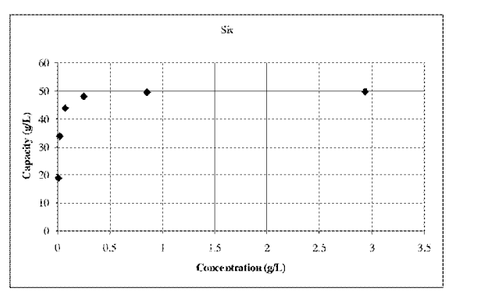
FIG. 7a shows the adsorption isotherm obtained using the six different separation matrix volumes of Example 1.
Figure 7B:
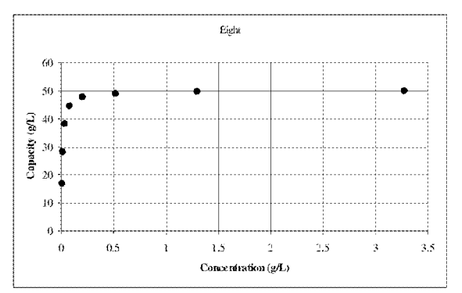
FIG. 7b shows the adsorption isotherm obtained using the eighth different separation matrix volumes of Example 1.
Figure 7C:
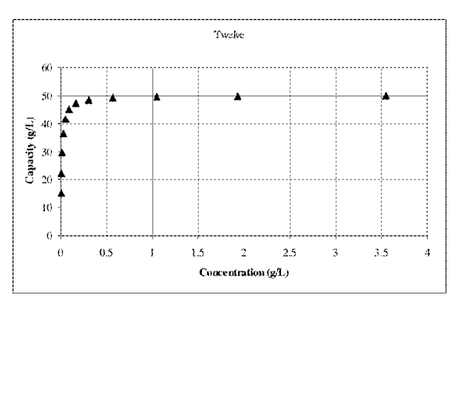
FIG. 7c shows the adsorption isotherm obtained using the twelve different separation matrix volumes of Example 1.

Examples of suitable resin distributions for the case when system volume is 200 uL and initial concentration is 4 g/L for a fairly typical protein adsorption characterize by Q max=50 g/L and K=0.01 g/L is given in Table E1 of FIG. 6. The isotherm that would be obtained using resin distributions form Table E1 are shown in FIGS. 7a, b and c.

The above experimental design can be further simplified. In the simplified version the design is based on geometrical series with a factor of 2, and with the second run location being performed at an initial concentration yielding the equilibrium concentration to be equal to the value of dissociation constant K. This design is thus characterize by the following relations (Eq. (5)), which upon substitution into Eqn. (1) and (2) characterize, will yield the new distribution of the solid phase.

$$C_i = K a^{i-2} \quad (5)$$

Following a similar logic the following modification to the simplified design can be also proposed, especially if the value of K is not really known.

$$C_i = \frac{C_{max}}{2^{i-1}} \quad (6)$$

where: $C_{max}$ is the highest available concentration of protein, and i is the run number.

Even though the present invention has been described above in terms of specific embodiments, many modification and variations of this invention can be made as will be obvious to those skilled in the art, without departing from its spirit and scope as set forth in the following claims.

What is claimed is:

1. A micro titre plate comprising a number of wells disposed in a plurality of columns and rows, the wells being filled with the same type of separation matrix having a series of volumes $V_1, V_2, \ldots V_n$ distributed according to a specific pattern of FIG. 1, 2, or 3 and FIG. 4.

2. The micro titre plate of claim 1 wherein the series of volumes $V_1, V_2, \ldots V_n$ is distributed according to a specific pattern for the calculation of an adsorption isotherm of the separation matrix such that the series of volumes results in a series of corresponding isotherm data points in the calculation of the adsorption isotherm.

3. The micro titre plate of claim 1, wherein each well in the plate has a permeable filter in the bottom.

4. A method for determining an adsorption isotherm comprising the steps of:
   using the micro titre plate of claim 1;
   adding the same volume and concentration of a liquid sample to the number of wells needed for the analysis;
   waiting for a predefined period of time until at least some of the sample is adsorbed onto the separation matrix; and
   measuring concentration of the sample remaining in the liquid phase and/or solid phase in at least two wells with different volumes of separation matrix.

5. The method of claim 4, wherein the predefined waiting time is until an equilibrium between the liquid and solid phases has been reached.

6. A method for determining an adsorption isotherm comprising the steps of:
   using a micro titre plate that comprises a number of wells disposed in a plurality of columns and rows, the wells being filled with the same type of separation matrix having a series of volumes $V_1, V_2, \ldots V_n$ distributed according to a specific pattern of FIG. 1, 2, or 3 and FIG. 4;
   adding the same volume and concentration of a liquid sample to the number of wells needed for the analysis;
   waiting for a predefined period of time until at least some of the sample is adsorbed onto the separation matrix; and
   measuring concentration of the sample remaining in the liquid phase and/or solid phase in at least two wells with different volumes of separation matrix.

* * * * *